(12) United States Patent
Ross

(10) Patent No.: US 6,301,716 B1
(45) Date of Patent: Oct. 16, 2001

(54) HEAD SUPPORT ASSEMBLY

(76) Inventor: Robert C. Ross, 701 Dougherty Pl., Flint, MI (US) 48504

( * ) Notice: Subject to any disclaimer, the term of this patent is extended or adjusted under 35 U.S.C. 154(b) by 0 days.

(21) Appl. No.: 09/625,133

(22) Filed: Jul. 25, 2000

Related U.S. Application Data

(60) Provisional application No. 60/146,496, filed on Jul. 30, 1999.

(51) Int. Cl.[7] .................................................. A41D 20/00
(52) U.S. Cl. ........................... 2/171; 2/171.8; 2/DIG. 11; 297/393
(58) Field of Search ............................. 297/39, 393, 397, 297/398, 399, 400, 464, 485, 468, 481, 466, 486, 406, 217; 128/846, 857; 2/171, 171.8, DIG. 11

(56) References Cited

U.S. PATENT DOCUMENTS

| | | | | |
|---|---|---|---|---|
| 2,726,714 | * | 12/1955 | McAndrews | 297/393 |
| 4,339,151 | * | 7/1982 | Riggs | 297/464 |
| 4,607,885 | * | 8/1986 | Fierro | 297/397 |
| 4,707,031 | * | 11/1987 | Meistrell | 297/393 |
| 5,081,714 | * | 1/1992 | Liu | 2/418 |

* cited by examiner

Primary Examiner—Gloria M. Hale
(74) Attorney, Agent, or Firm—Howard & Howard

(57) ABSTRACT

A head support assembly to facilitate the care of a physically disabled individual. The head support assembly includes a headpiece and an attachment cord attached to the headpiece which is adapted to be attached to a chair etc. The attachment cord and headpiece provide resilient support for an individual's head to facilitate the care of the individual.

12 Claims, 2 Drawing Sheets

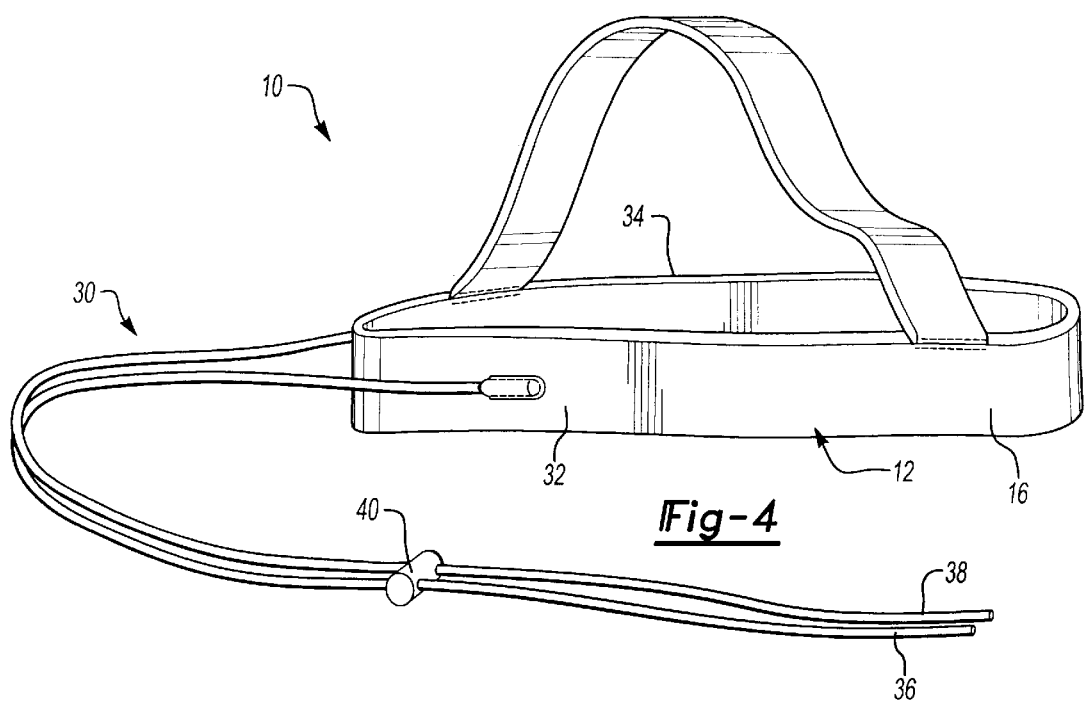

HEAD SUPPORT ASSEMBLY

This patent application claims priority from its provisional patent application, Ser. No. 60/146,496, filed Jul. 30, 1999.

BACKGROUND

The present invention relates to a head support assembly and more particularly to a head support assembly used to securely hold the head of a disabled person without undue restraint.

Individuals with poor musculoskeletal control find it difficult or are even unable to hold their heads for feeding, drinking, washing etc. In order to care for these people, the caregiver typically has to hold the individual's head up by hand. Fixed restraints are not acceptable because they can be invasive and uncomfortable and in most jurisdictions are not permitted.

SUMMARY OF THE INVENTION

The present invention overcomes the above problem by providing a head support assembly that includes a headpiece with an attachment cord having one end attached to the headpiece. The other end of the attachment cord is adapted to be connected to a fixed object, such as for example a chair back. The attachment cord is resilient and provides secure support for an individual's head to facilitate the care of the disabled individual but still allow for movement of the head. The resiliency of the attachment cord allows the individual's head to move about freely but still be held in an upright position.

In the preferred embodiment, the headpiece includes a headband that fits about the individual's head. Preferably, the headband is adjustable and in the disclosed embodiment a hook and loop type fastener such as a Velcro® before words fastener is used. As one of ordinary skill will appreciate, other fasteners will work such as a buckle, slide clasp etc. The headpiece also includes a head strap that extends over the top of the individual's head. The head strap keeps the feeding cap from sliding down on the individual's face.

The attachment cord is connected to the headpiece for example by sewing the cord directly to the headband. In one embodiment the cord includes a clasp that allows for adjustment of the cord with respect to the chair back.

BRIEF DESCRIPTION OF THE DRAWINGS

FIG. 4 is a perspective view of another embodiment of the present invention.

DETAILED DESCRIPTION OF THE PRESENT INVENTION

Figure 1:
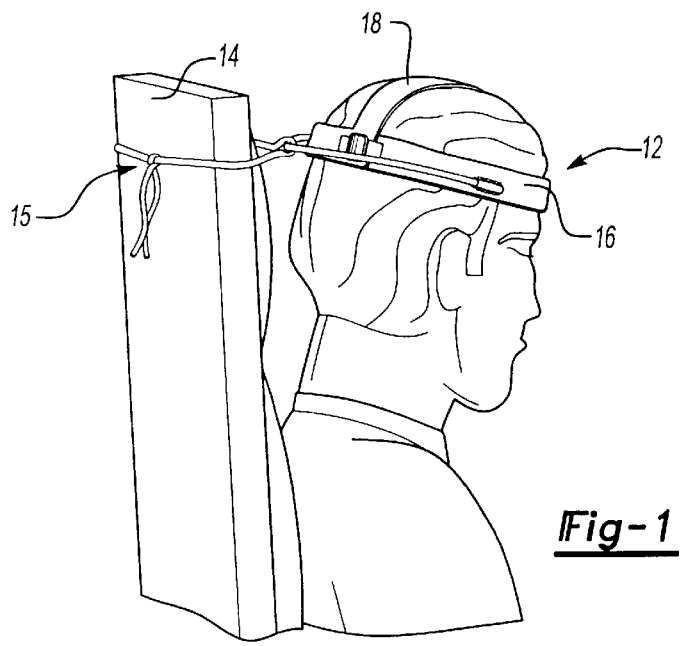
FIG. 1 is a side view of the head support assembly of the present invention positioned upon a disabled individual.

The head support assembly of the present invention is shown generally at 10 in FIGS. 1 through 4. The head assembly 10 includes a headpiece 12 and attachment cord 15. As illustrated, the attachment cord 15 is connected to a chair 14 to hold the individual's head up, but still allow movement of the individual's head.

The headpiece 12 includes a headband 16 and a head strap 18. The headband 16 is preferably adjustable through the use of a loop and hook type connector 19. As will be appreciated, any type of adjustable fastener could be used such as for example a buckle, sliding clasp, etc. The head strap 18 keeps the feeding cap from sliding down on the individual's face. In the preferred embodiment, the headband 16 and head strap 18 are made of vinyl for comfort and to facilitate cleaning. A cloth type cover 21 is used to provide more comfort to the user. The cover 21 covers the headband 16 and strap 18. The headband 16 and head strap 18 are preferably sewn together. It should be appreciated that other types of headpieces could be used, such as for example a full cap, but the disclosed headpiece 12 is preferred.

Figure 2:
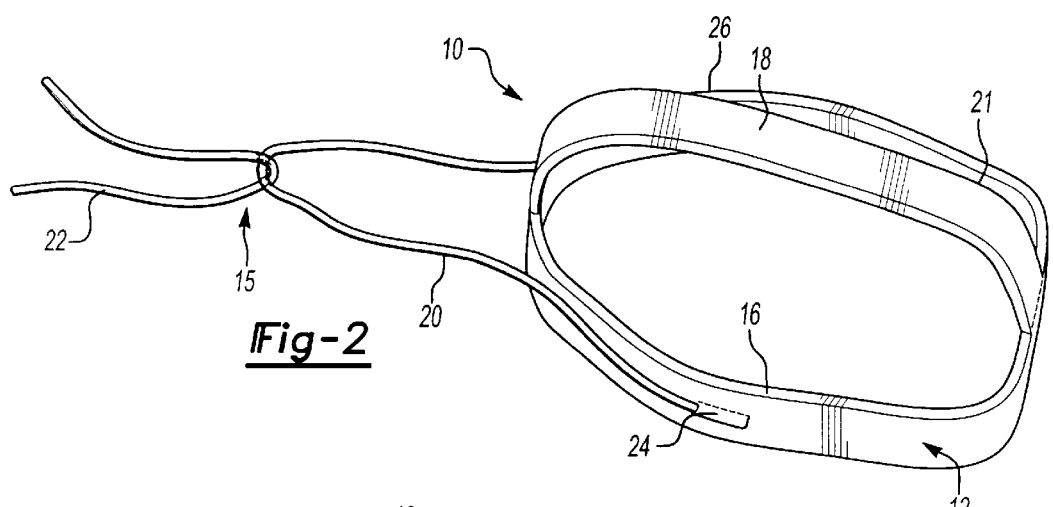
FIG. 2 is a perspective view of an embodiment of the present invention.
Figure 3:
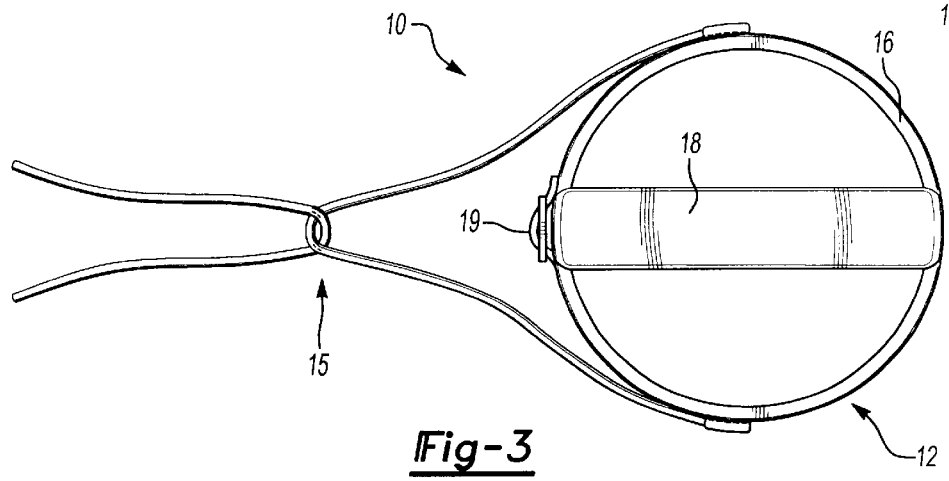
FIG. 3 is a top view of the head support assembly of the present invention.

The attachment cord 15 of the embodiment illustrated in FIGS. 2 and 3 includes a cord 20, preferably a nylon cord, which is sewn to the head band 16 and a resilient cord 22, which is a bungie type cord, that is connected to the nylon cord 20. In the disclosed embodiment, the bungie type cord 22 is tied to the nylon cord 20 and tied behind chair 14. As will be appreciated, other methods of connecting the bungie type cord 22 to the chair 14 and cord 20 are available. The attachment cord 15 is preferably sewn to the sides 24 and 26 of the headband 16.

With reference to FIG. 4, another embodiment of the present invention is illustrated. In this embodiment, the headpiece 12 is the same as the headpiece illustrated in FIGS. 1 through 3. This embodiment differs in the type of attachment cord that is used. In this embodiment, the attachment cord 30 is made of a single elastic nylon material. The ends are attached to the sides 32 and 34 of the headband 16. The opposite ends 36 and 38 are connected together, such as by tying the ends together or as will be appreciated by making the cord 30 a single length of cord. A cord stop 40 is provided to facilitate attachment to the chair 14. In use, the cord 30 is placed over the back of chair 14 and the cord stop 40 is tightened against the chair 14 to connect the headpiece 12 to the chair.

With respect to the embodiment illustrated in FIGS. 1 through 3, the headpiece 12 is positioned over the individual's head as illustrated in FIG. 1. The headband 16 is positioned around the forehead, back and sides of the head and the head strap 18 is positioned across the top of the head and extends preferably from the front to the back of the individual's head. The attachment cord 15 and in particular the resilient portion 22 is then connected to the back of chair 14 upon which the individual is seated. Because of the resiliency in the cord 22, the individual's head is allowed to move about fairly freely while still being held in the upright position. The head support assembly in FIG. 4 is used in the same way with the exception that the attachment cord 30 is placed around the back of the individual's chair and then the cord stop 40 is positioned to hold the attachment cord 30 in place. This is done by sliding the attachment stop 40 closer to the chair to prevent the attachment cord 30 from slipping off of the chair 14. The stop 40 can also be used to adjust the length of cord 30 by moving cord stop 40 with respect to chair 14.

Other aspects, objects and advantages of this invention can be obtained from a study of the drawings, the disclosure and the appended claims.

What is claimed is:

1. A head support assembly to facilitate the care of a physically disabled individual, said head support assembly comprising:

a headpiece;

an attachment cord attached to the headpiece and adapted to be attached to a fixed object;

said attachment cord and headpiece providing resilient support for an individual's head to facilitate the care of a disabled individual, said cord and headpiece permitting free movement of a user's head throughout the normal range of movement while holding the user's head in a generally upright position to prevent the user's head from falling forward onto the user's chest.

2. The head support assembly of claim 1, wherein said headpiece includes a headband adapted to fit about an individual's head.

3. The head support assembly of claim 2, wherein said headband is adjustable.

4. The head support assembly of claim 2, wherein said headpiece includes a head strap.

5. The head support assembly of claim 3, wherein said headband includes a headstrap.

6. The head support assembly of claim 1, wherein said attachment cord is resilient providing support for the individual's head while permitting movement of the individual's head.

7. The head support assembly of claim 1, wherein said attachment cord includes an adjustment device to adjust the attachment cord and secure the head support to the fixed support.

8. The head support assembly of claim 1, wherein said attachment cord includes first and second ends, each attached to said headpiece to define a closed loop.

9. The head support assembly of claim 8, wherein said attachment cord includes an adjustment device to adjust said attachment cord and secure the head support to the fixed support, said attachment cord including first and second portions, said adjustment device joining said first and second portions.

10. A head support assembly to facilitate the care of a physically disabled individual, said head support assembly comprising:

a headpiece;

an attachment cord attached to the headpiece and adapted to be attached to a fixed object;

said attachment cord and headpiece providing resilient support for an individual's head to facilitate the care of a disabled individual, said attachment cord includes an adjustment device to adjust said attachment cord and secure the head support to the fixed support, said attachment cord including first and second portions, said adjustment device joining said first and second portions.

11. The head support assembly of claim 10, wherein said adjustment device slides along said first and second portions to adjust the length of said adjustment cord between the fixed support and said head support assembly.

12. The head support assembly of claim 10, wherein said attachment cord includes a nylon cord interconnected to a resilient cord.

* * * * *